(12) United States Patent
Kleis (10) Patent No.: US 12,419,774 B2
(45) Date of Patent: Sep. 23, 2025

(54) HUMERAL FRACTURE BRACE ASSEMBLY AND ASSOCIATED METHODS

(71) Applicant: Keith Kleis, Tarpon Springs, FL (US)

(72) Inventor: Keith Kleis, Tarpon Springs, FL (US)

( * ) Notice: Subject to any disclaimer, the term of this patent is extended or adjusted under 35 U.S.C. 154(b) by 190 days.

(21) Appl. No.: 18/466,448

(22) Filed: Sep. 13, 2023

(65) Prior Publication Data

US 2025/0082490 A1    Mar. 13, 2025

(51) Int. Cl.
  *A61F 5/058*  (2006.01)
(52) U.S. Cl.
  CPC ............... *A61F 5/05858* (2013.01)
(58) Field of Classification Search
  CPC ............ A61F 5/05858; A61F 5/0585; A61F 5/05841; A61F 5/05866; A61F 5/05875; A61F 5/05; A61F 5/058; A61F 5/05833; A61F 5/04
  See application file for complete search history.

(56) References Cited

U.S. PATENT DOCUMENTS 5,171,310 A * 12/1992 Chisena .............. A61F 5/05841
                                                 602/5
5,286,249 A *  2/1994 Thibodaux ............ A61F 5/0125
                                                 602/5
5,546,942 A *  8/1996 Zhang .................... G16H 20/40
                                                 700/262
2013/0184627 A1* 7/2013 Vedder ............... A61B 17/1739
                                                 602/20

FOREIGN PATENT DOCUMENTS

CN            116153173 A   *   5/2023

* cited by examiner

*Primary Examiner* — Tarla R Patel
(74) *Attorney, Agent, or Firm* — Jonathan D Staudt; Widerman Malek, PL (57) ABSTRACT

The humeral fracture brace assembly and method are for immobilizing a humeral bone fracture of a patient. The humeral fracture brace assembly includes an elongated cuff, which wraps and surrounds the bicep area of the patient to immobilize the bones of the humeral bone fracture. The elongated cuff is constructed with a semi-rigid sheet and an associated pad for comfort. Trim indicators are provided on the cuff to indicate trimmable areas for adjusting its dimensions. The assembly also includes a plurality of straps and strap loops anchored on the outside of the cuff, allowing for tightening when wrapped around the bicep area. Additionally, removable bolsters are positioned and attached to the inside of the cuff at specific positions relative to the humeral bone fracture.

16 Claims, 6 Drawing Sheets

HUMERAL FRACTURE BRACE ASSEMBLY AND ASSOCIATED METHODS

FIELD OF THE INVENTION

The present invention relates to fracture braces and methods, and more specifically to a humeral fracture brace and associated methods.

BACKGROUND

A variety of bone fractures can occur in various regions of the body. Bone fractures can occur, e.g., in the arm, involving the humerus and/or forearm and/or wrist; in the leg, involving the tibia and/or fibula; or at, in, or near articulating condyles (also called a condular fracture), e.g. at, in, or near the elbow, or at, in, or near the knee.

Under most circumstances bone fractures may be treated with immobilization. For example, Type 1 fractures are un-displaced or minimally displaced fractures, such as hairline fractures and are treated with immobilization in a cast/brace without any manipulation. Type 2 fractures are partially displaced such that the regions are nearly aligned, with some bony contact present. This type is typically treated by manipulation followed by immobilization in a cast/brace.

Non-surgical treatment is significantly less expensive and involves lower risk. Distal third and midshaft humeral fractures have been treated non-surgically using known humeral fracture braces, such as a Sarmiento style brace. See Sarmiento A, Kirman P B, Galvin E G, Schmitt R H, Phillips J G, "Functional Bracing of Fractures of the Shaft of the Humerus," J. Bone Joint Surg. (Am) 1977; 59A; 596-601.

U.S. Pat. No. 5,383,844 to Munoz et al. is directed to a humeral fracture brace which includes a humeral cuff that is pivotally connected to a forearm support by a sliding hinge that allows the forearm support to slide relative to the axis of the humeral cuff. The humeral support is formed of a circumferential cuff which has a pair of tensioning straps for allowing differential compressive connections to the humerus.

However, humeral fractures often heal with significant angular deformity. And, many of the existing braces often pinch tissue and are difficult for a patient to apply without assistance.

Accordingly, it may be desired to provide a size-adjustable humeral fracture brace to immobilize fractures while also reducing the angle of the fracture, and which is easier for a patient to don and doff without assistance.

This background information is provided to reveal information believed by the applicant to be of possible relevance to the present invention. No admission is necessarily intended, nor should be construed, that any of the preceding information constitutes prior art against the present invention.

SUMMARY OF THE EMBODIMENTS

An object of the present invention may be to provide a humeral fracture brace assembly and method that offer advantages such as improved immobilization, comfort, and adjustability. The use of trim indicators allows for customization of the cuff's dimensions, and the removability of bolsters provides flexibility and proper alignment. The assembly's design and materials, such as the semi-rigid sheet and associated pad, enhance rigidity and patient comfort.

Objects and features of the invention may be provided by a humeral fracture brace assembly and a method for immobilizing a humeral bone fracture of a patient. The humeral fracture brace assembly comprises an elongated cuff, which wraps and surrounds the bicep area of the patient to immobilize the bones of the humeral bone fracture. The elongated cuff is constructed with a semi-rigid sheet and an associated pad for comfort. Trim indicators are provided on the cuff to indicate trimmable areas for adjusting its dimensions. The assembly also includes a plurality of straps and strap loops anchored on the outside of the cuff, allowing for tightening when wrapped around the bicep area. Additionally, removable bolsters are positioned and attached to the inside of the cuff at specific positions relative to the humeral bone fracture.

The method for immobilizing a humeral bone fracture involves providing the humeral fracture brace assembly, measuring the bicep area of the patient, trimming the elongated cuff based on the measurements, positioning and attaching the bolsters, wrapping the brace around the bicep area, and tightening the brace using the straps and strap loops until snug. The method ensures a customized fit and immobilization of the humeral bone fracture.

BRIEF DESCRIPTION OF THE DRAWINGS

The example embodiments are best understood from the following detailed description when read with the accompanying drawing figures. In fact, the dimensions may be arbitrarily increased or decreased for clarity of discussion. Wherever applicable and practical, like reference numerals refer to like elements.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

Objectives of the embodiments may include: to wrap around the bicep area squeezing all sides of the fracture site to immobilize the bones; to use bolsters to press on the three points of leverage to assist reducing the angle of the fracture; for the patient to be able to don and doff the brace without assistance if necessary; and the length and width can be cut to customize the fit of the brace to better match the patient's anatomy. Trimming the length and or width may make for a more accurate and comfortable fit. Using the bolsters may reduce the angle of acceptability of the fracture and keeps constant pressure on the points of leverage. Also, the one piece wrap-around brace should be easier for patients to remove and apply without assistance.

FIGS. 1-6 illustrate an example embodiment of a humeral fracture brace assembly 10 according to features of the present invention. The brace 10 is configured to immobilize a humeral bone fracture of a patient. The humeral fracture brace assembly 10 includes an elongated cuff 12 comprising a semi-rigid sheet 14 and associated pad 16. The elongated cuff 12 is configured to wrap and surround a bicep area of a patient to immobilize bones of a humeral bone fracture. The elongated cuff 12 may more rigid in a height direction transverse to its length.

The semi-rigid sheet 14 may include a plastic material that provides rigidity when the elongated cuff 12 is wrapped around the bicep area of the patient. The associated pad 16 may extend the length of the elongated cuff 12 and is formed of a material that provides a comfortable skin interface when the elongated cuff 12 is wrapped around the bicep area of the patient.

A plurality of trim indicators 18 are adjacent or near at least one edge of the elongated cuff 12. The trim indicators 18 may be adjacent both ends or edges of the elongated cuff 12 (although not shown). The trim indicators 18 are configured to indicate trimmable areas for adjusting dimensions of the elongated cuff 12. Soft tape 20 is included and is configured to cover the edges of the elongated cuff 12 after trimming.

A plurality of straps 22 are anchored (e.g. via rivets 26) on an outside of the elongated cuff 12. A plurality of strap loops 24 are also anchored (e.g. via rivets 28) on the outside of the elongated cuff 12 and configured to receive one of the straps 24 therethrough to tighten the elongated cuff 12 when wrapped around the bicep area of the patient. The plurality of straps 22 are preferably hook-and-loop fasteners. As such, the ends of the straps 22 may include the hook portion 23 of the hook-and-loop fasteners. The plurality of straps 22 and plurality of strap loops 24 may be anchored to the outside of the elongated cuff 12 with at least one of stitching, rivets, grommets, heat welds and adhesive, for example.

Figure 1:
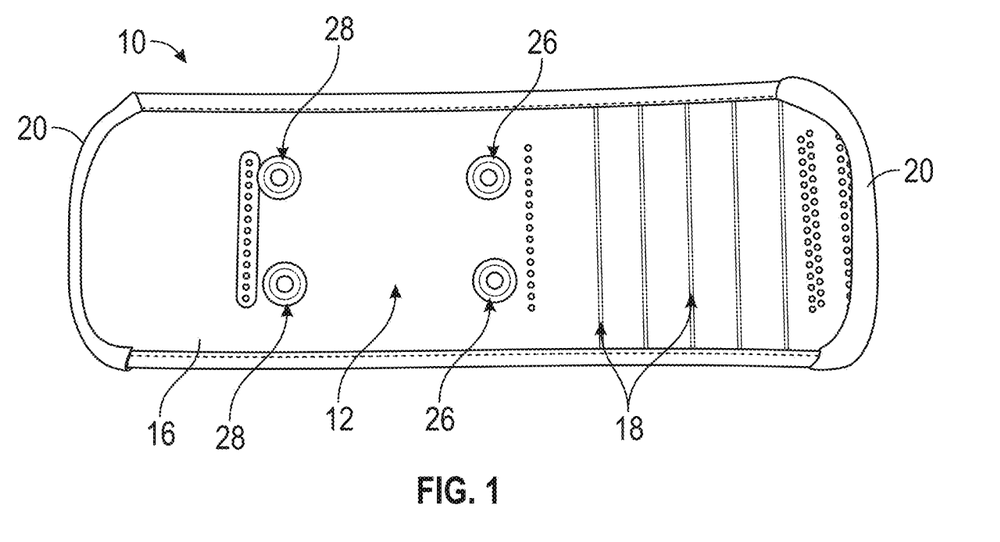
FIG. 1 is an inside view illustrating an example embodiment of a humeral fracture brace assembly in accordance with features of the present invention.
Figure 2:
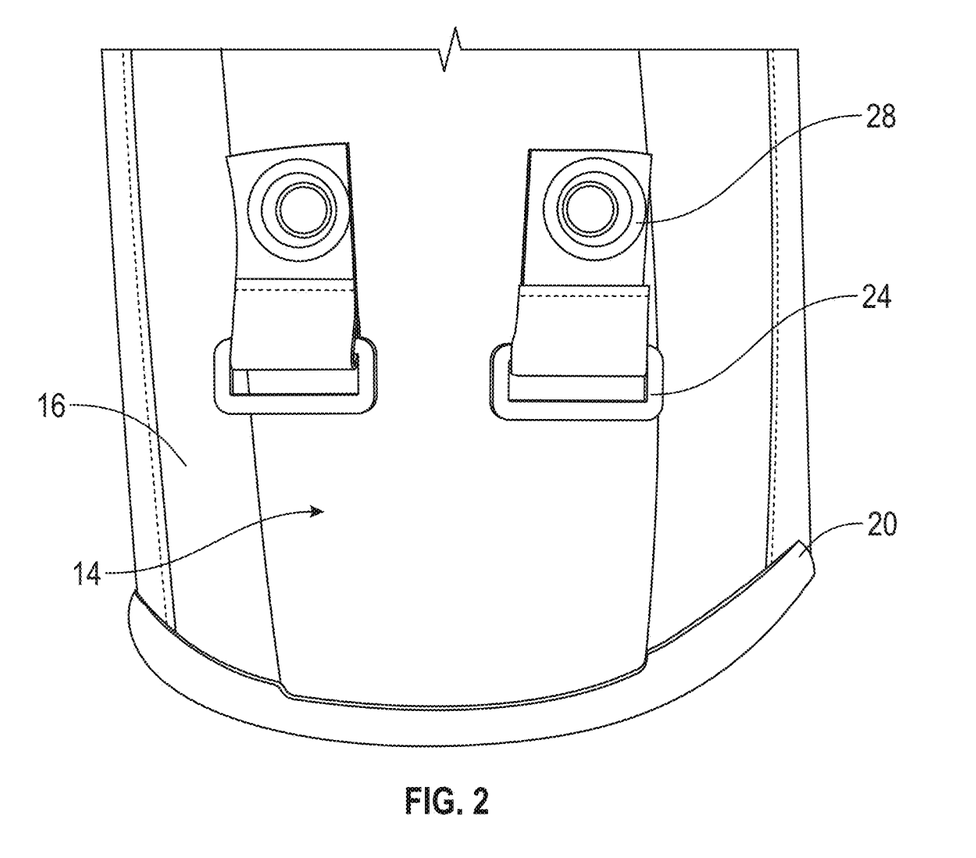
FIG. 2 is a outside view illustrating details of a portion of the humeral fracture brace assembly of FIG. 1.
Figure 3:
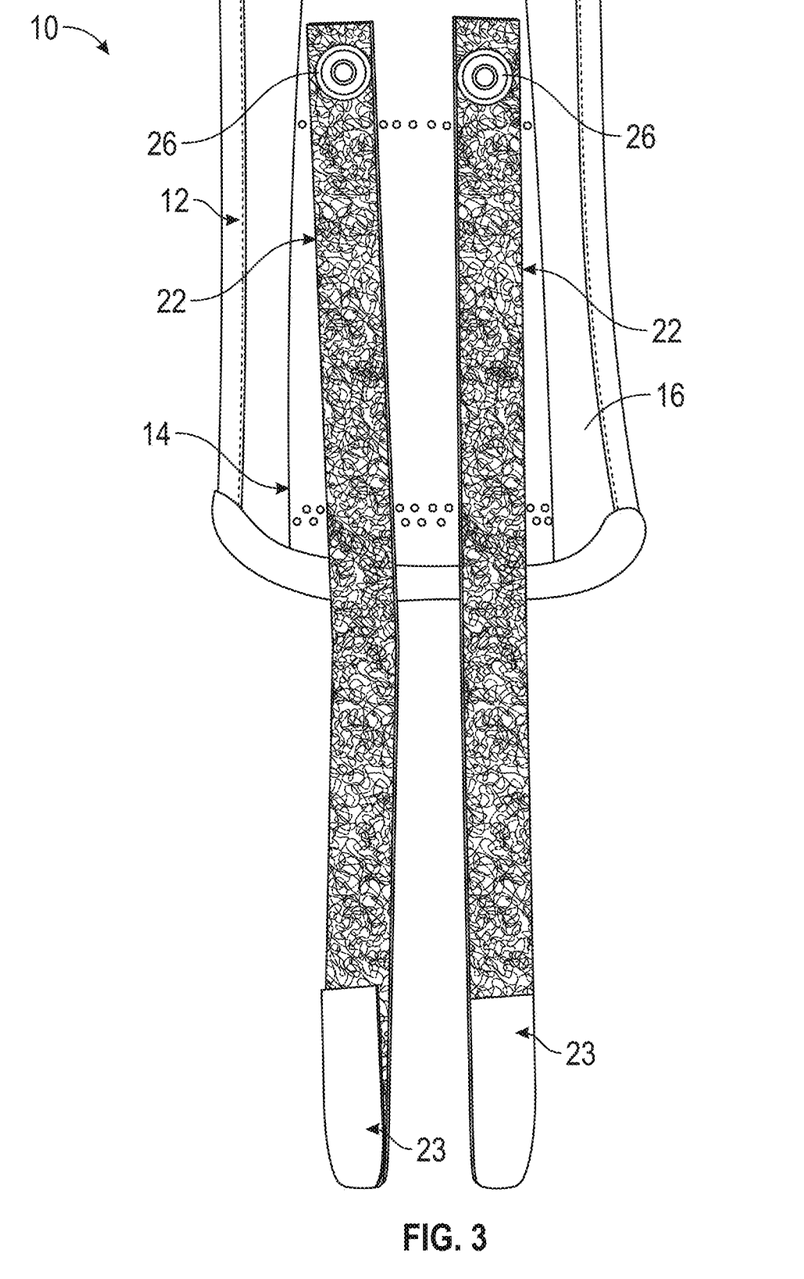
FIG. 3 is another outside view illustrating details of another portion of the humeral fracture brace assembly of FIG. 1.
Figure 4:
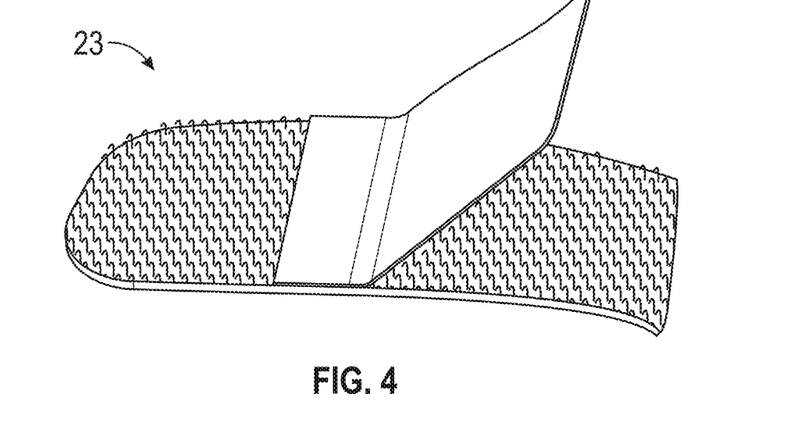
FIG. 4 is a perspective view illustrating details of an alligator hook-and-loop fastener of the humeral fracture brace assembly of FIG. 1.

As illustrated in FIG. 4, the hook portion 23 may be an alligator hook-and-loop portion so that the straps 22 can be cut based upon the circumference of the arm, and the hook portion 23 re-positioned on the cut end of the strap 22.

Figure 5:
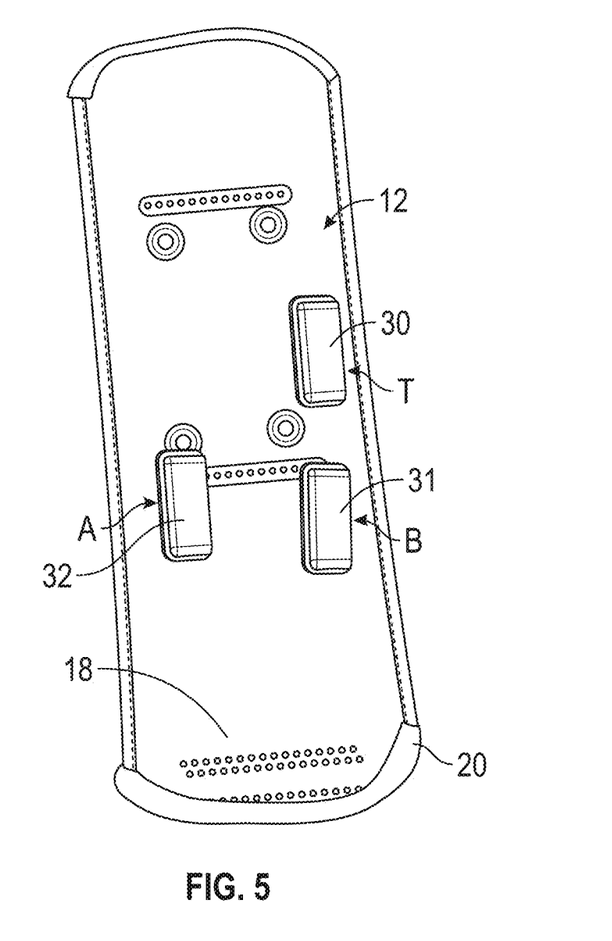
FIG. 5 is an inside view illustrating further details of the humeral fracture brace assembly of FIG. 1.
Figure 6:
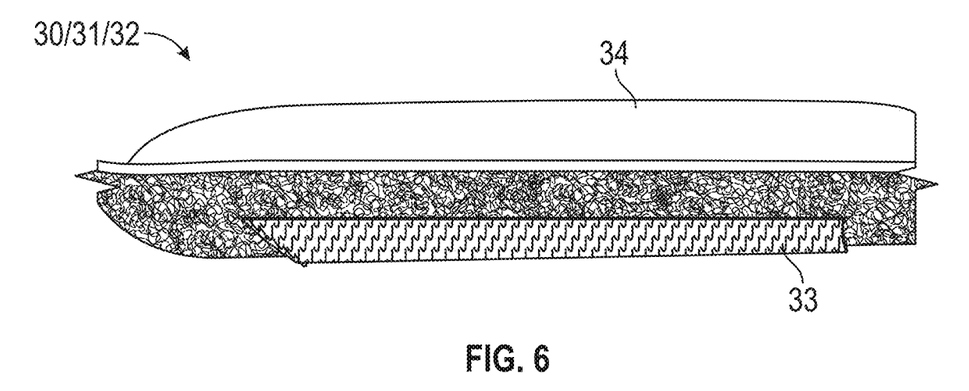
FIG. 6 is an side view illustrating details of the bolsters of the humeral fracture brace assembly of FIG. 1.
Figure 7:
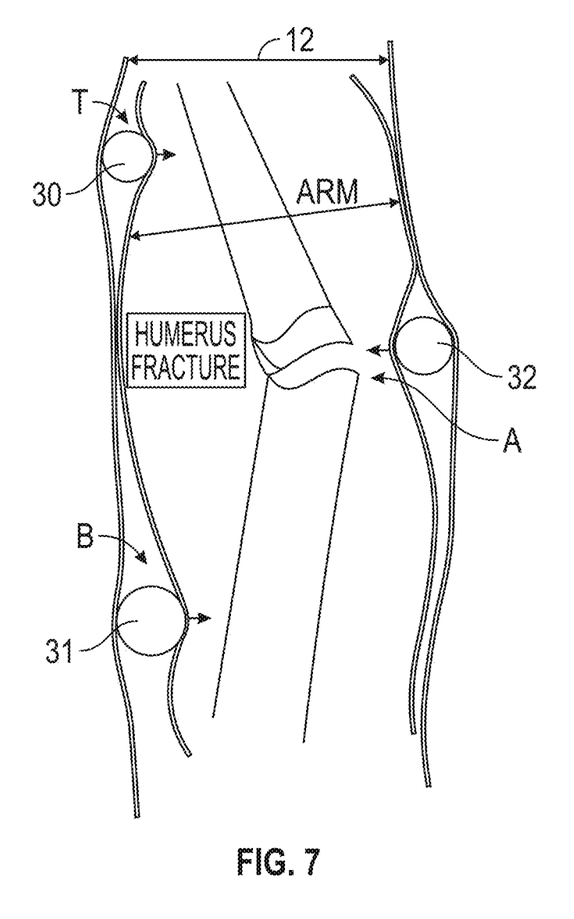
FIG. 7 is a cross-sectional view illustrating the humeral fracture brace assembly of FIG. 1 applied to a humeral fracture of an arm.
Figure 8:
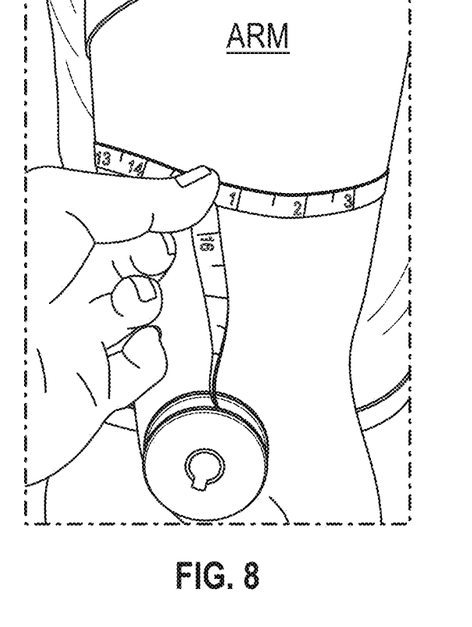
FIG. 8 is a perspective view of a measuring step in accordance with applying the humeral fracture brace assembly of FIG. 1.
Figure 9:
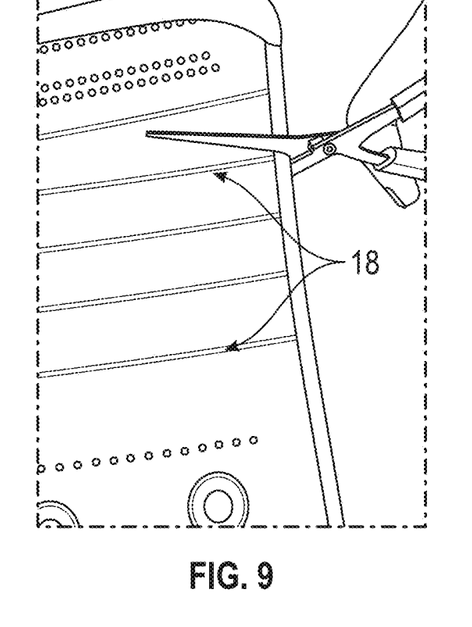
FIG. 9 is a perspective view of a trimming step in accordance with applying the humeral fracture brace assembly of FIG. 1.
Figure 10:
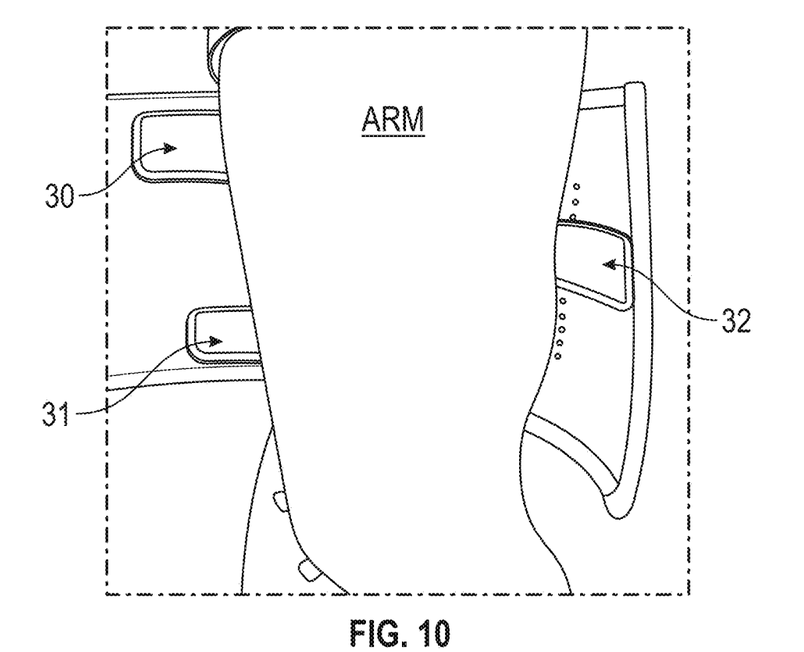
FIG. 10 is a perspective view of an installation step in accordance with applying the humeral fracture brace assembly of FIG. 1.
Figure 11:
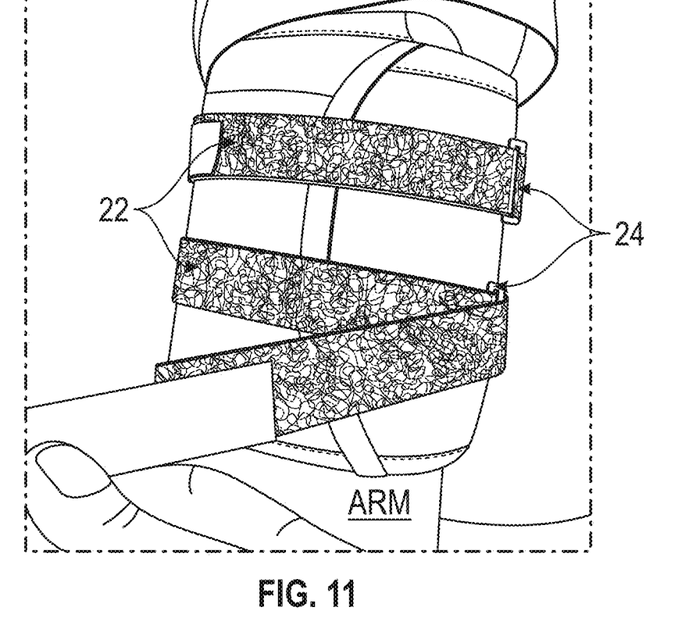
FIG. 11 is a perspective view of a strap tightening step in accordance with applying the humeral fracture brace assembly of FIG. 1.
Figure 12:
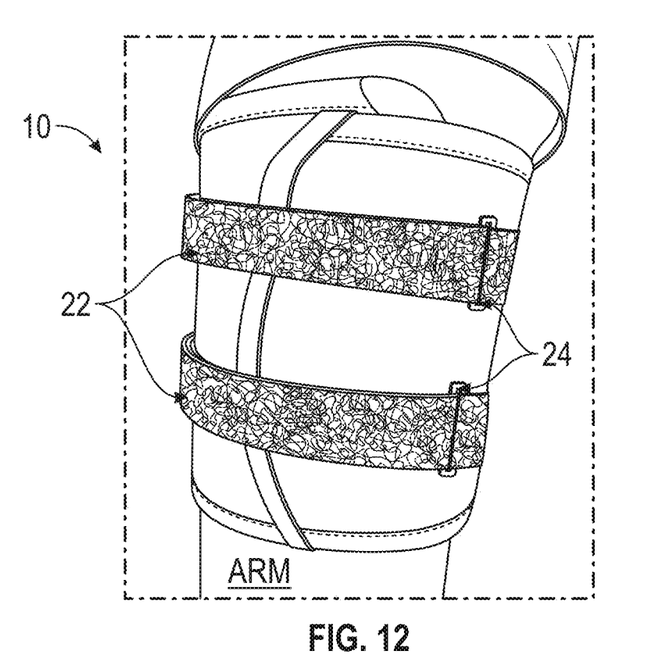
FIG. 12 is a perspective view of the humeral fracture brace assembly of FIG. 1 installed on an arm.

Referring more specifically to FIGS. 5-7, bolsters 30/31/32 will now be described. A first bolster 30 is configured to removably attach to an inside of the elongated cuff 12 at a top base position T adjacent a top end of the humeral bone fracture when the elongated cuff is wrapped around the bicep area of the patient. A second bolster 31 is configured to removably attach to the inside of the elongated cuff 12 at a bottom base position B adjacent a bottom end of the humeral bone fracture when the elongated cuff is wrapped around the bicep area of the patient; a third bolster 32 is configured to removably attach to the inside of the elongated cuff 12 at an apex position A adjacent an apex of the humeral bone fracture when the elongated cuff 12 is wrapped around the bicep area of the patient. The bolsters 30/31/32 may include an attachment side 33 for removably attaching to the inside of the elongated cuff 12, and include an arm-interface side 34 for alignment of the humeral bone fracture.

Referring additionally to FIGS. 8-12, a method to immobilize a humeral bone fracture of a patient is described. The method includes: providing a humeral fracture brace assembly 10 as described above; measuring the bicep area of the patient (FIG. 8); trimming the elongated cuff 12 based upon measurements (FIG. 9); positioning and attaching the first, second and third bolsters 30/31/32 on the inside of the elongated cuff 12 before wrapping the humeral fracture brace around the bicep area of the patient (FIG. 10); and feeding the straps 22 through the strap loops 24 to tighten the humeral facture brace assembly 10 until snug.

An example embodiment is now described. As discussed, the brace assembly 10 is a wrap that surrounds the bicep in order to immobilize a fractured humerus. The brace 10 may be manufactured in a few off-the-shelf (OTS) sizes, each size capable of being cut, trimmed and modified to fit a variety of patients. The size described here is for a large adult. The length and width of the materials may change for other sizes but the structure may generally remain the same.

The foundation is a semi rigid pad 16 capable of holding its shape when wrapping around the arm. It may be approximately eight inches by eighteen inches, for example. Its width may be trimmed to fit a shorter humerus as well as shaping it to the axilla and antecubital areas. The length can be shortened for a thinner arm, with lines marked and labeled at least at one end of the interior of the brace assembly 10 for the amount to be trimmed off. A fleece style tape 20 is included to cover the cut edges. The inside lining of the brace assembly 10 may be of a material that will allow hook-and-loop fasteners to adhere to it so that bolsters 30/31/32 may be placed in strategic areas.

A semi rigid thin sheet 14 of plastic type material is attached to the exterior of the padding running the length of the brace assembly 10. This allows the brace to remain rigid area while being tightened around the arm and fracture. Its width may be approximately five and a half inches, for example, leaving about one and a quarter inch of padding on each side for trimming and comfort.

At least two straps 22 and two loops 24 are attached to the exterior of the brace for the purpose of tightening the brace. The straps 22 may be anchored by any sturdy means, including stitching, rivets, grommets etc. The loops 24 may be anchored so that the eyes are approximately 2 inches from the end of the brace assembly 10 opposite the sizing hashmarks on the interior lining, with the eyes laying towards that end. The straps 22 may be anchored approximately one inch away from the loops 24 laying towards the end of the brace assembly 10 with the sizing hash marks on the interior side. These straps 22 are about twenty inches long and equipped with alligator hook-and-loop fasteners 23 (e.g. Velcro®) so that the straps 22 can be cut to accommodate the circumference of the arm. The straps 22 for this particular size may be one and a half inches in width.

Three bolsters 30/31/32 may be included with the brace assembly 10. These are small rectangular pieces of firm foam, rubber, or gel. They are approximately 1"×2"×¼" with one flat side 33 to lay against the inside of the brace assembly 10 with hook portions of hook-and-loop fasteners attaching it, for example. All other corners are preferably rounded to avoid discomfort against the patient's skin. The bolsters 30/31/32 are placed at the apex A of the fracture and the ends T/B of the bone opposite the apex as illustrated in FIG. 7. The bolsters 30/31/32 can be removed if the fracture alignment is acceptable and needs no further reducing.

The application of the brace assembly 10 starts with measuring the circumference of the arm at the belly of the biceps. The brace assembly 10 is then cut to the proper length at the appropriate hash mark, and the cut end covered with the fleece tape 20. The bolsters 30/31/32 are placed at the apex A, top T and base B of the fracture. The brace assembly 10 is wrapped around the arm with the recently cut end sliding under the end with the loops 24, the straps 22 are fed through the loops 24, and the straps 22 may be shortened with reapplication of the alligator ends 23. The straps 22 are tightened so that the brace assembly 10 is snug against the patient's arm without causing numbness and tingling.

The present invention may have also been described, at least in part, in terms of one or more embodiments. An embodiment of the present invention is used herein to illustrate the present invention, an aspect thereof, a feature thereof, a concept thereof, and/or an example thereof. A physical embodiment of an apparatus, an article of manufacture, a machine, and/or of a process that embodies the present invention may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

The above description provides specific details, such as material types and processing conditions to provide a thorough description of example embodiments. However, a person of ordinary skill in the art would understand that the embodiments may be practiced without using these specific details.

Some of the illustrative aspects of the present invention may be advantageous in solving the problems herein described and other problems not discussed which are discoverable by a skilled artisan. While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item. Thus, the scope of the invention should be determined by the appended claims and their legal equivalents, and not by the examples given.

The invention claimed is:

1. A humeral fracture brace assembly configured to immobilize a humeral bone fracture of a patient, the humeral fracture brace assembly comprising:
    an elongated cuff comprising a semi-rigid sheet and associated pad, and configured to wrap and surround a bicep area of the patient to immobilize bones of the humeral bone fracture, the elongated cuff being more rigid in a height direction transverse to its length;
    trim indicators on at least one edge of the elongated cuff configured to indicate trimmable areas for adjusting dimensions of the elongated cuff;
    a plurality of straps anchored on an outside of the elongated cuff;
    a plurality of strap loops anchored on the outside of the elongated cuff and configured to receive one of the straps therethrough to tighten the elongated cuff when wrapped around the bicep area of the patient;
    a first bolster configured to removably attach to an inside of the elongated cuff at a top base position adjacent a top end of the humeral bone fracture when the elongated cuff is wrapped around the bicep area of the patient;
    a second bolster configured to removably attach to the inside of the elongated cuff at a bottom base position adjacent a bottom end of the humeral bone fracture when the elongated cuff is wrapped around the bicep area of the patient;
    a third bolster configured to removably attach to the inside of the elongated cuff at an apex position adjacent an apex of the humeral bone fracture when the elongated cuff is wrapped around the bicep area of the patient.

2. The humeral fracture brace assembly according to claim 1, wherein the semi-rigid sheet comprises a plastic material that provides rigidity when the elongated cuff is wrapped around the bicep area of the patient.

3. The humeral fracture brace assembly according to claim 1, wherein the associated pad extends the length of the elongated cuff and comprises a material that provides a comfortable skin interface when the elongated cuff is wrapped around the bicep area of the patient.

4. The humeral fracture brace assembly according to claim 1, wherein the trim indicators are on two edges of the elongated cuff and configured to indicate trimmable areas for adjusting the length and height of the elongated cuff.

5. The humeral fracture brace assembly according to claim 4, further comprising soft tape configured to cover the two edges after trimming.

6. The humeral fracture brace assembly according to claim 1, wherein the plurality of straps include hook-and-loop fasteners.

7. The humeral fracture brace assembly according to claim 1, wherein the plurality of straps and plurality of strap loops are anchored to the outside of the elongated cuff with at least one of stitching, rivets, grommets, heat welds and adhesive.

8. The humeral fracture brace assembly according to claim 1, wherein the first, second and third bolsters include an attachment side for removably attaching to the inside of the elongated cuff, and include an arm-interface side for alignment of the humeral bone fracture.

9. A method to immobilize a humeral bone fracture of a patient, the method comprising:
 providing a humeral fracture brace assembly comprising
  an elongated cuff comprising a semi-rigid sheet and associated pad, and configured to wrap and surround a bicep area of the patient to immobilize bones of the humeral bone fracture, the elongated cuff being more rigid in a height direction transverse to its length;
  trim indicators on at least one edge of the elongated cuff configured to indicate trimmable areas for adjusting dimensions of the elongated cuff;
  a plurality of straps anchored on an outside of the elongated cuff;
  a plurality of strap loops anchored on the outside of the elongated cuff and configured to receive one of the straps therethrough to tighten the elongated cuff when wrapped around the bicep area of the patient;
  a first bolster configured to removably attach to an inside of the elongated cuff at a top base position adjacent a top end of the humeral bone fracture when the elongated cuff is wrapped around the bicep area of the patient;
  a second bolster configured to removably attach to the inside of the elongated cuff at a bottom base position adjacent a bottom end of the humeral bone fracture when the elongated cuff is wrapped around the bicep area of the patient;
  a third bolster configured to removably attach to the inside of the elongated cuff at an apex position adjacent an apex of the humeral bone fracture when the elongated cuff is wrapped around the bicep area of the patient;
 measuring the bicep area of the patient;
 trimming the elongated cuff based upon measurements;
 positioning and attaching the first, second and third bolsters on the inside of the elongated cuff;
 wrapping the humeral fracture brace around the bicep area of the patient; and
 feeding the straps through the strap loops to tighten the humeral facture brace assembly until snug.

10. The method according to claim 9, wherein the semi-rigid sheet comprises a plastic material that provides rigidity when the elongated cuff is wrapped around the bicep area of the patient.

11. The method according to claim 9, wherein the associated pad extends the length of the elongated cuff and comprises a material that provides a comfortable skin interface when the elongated cuff is wrapped around the bicep area of the patient.

12. The method according to claim 9, wherein the trim indicators are on two edges of the elongated cuff and configured to indicate trimmable areas for adjusting the length and height of the elongated cuff.

13. The method according to claim 12, further comprising applying soft tape to cover the two edges after trimming.

14. The method according to claim 9, wherein the plurality of straps include hook-and-loop fasteners.

15. The method according to claim 9, wherein the plurality of straps and plurality of strap loops are anchored to the outside of the elongated cuff with at least one of stitching, rivets, grommets, heat welds and adhesive.

16. The method according to claim 9, wherein the first, second and third bolsters include an attachment side for removably attaching to the inside of the elongated cuff, and include an arm-interface side for alignment of the humeral bone fracture.

\* \* \* \* \*